April 30, 1940. C. A. CHASE Plant Pat. 383
ROSE
Filed June 20, 1939
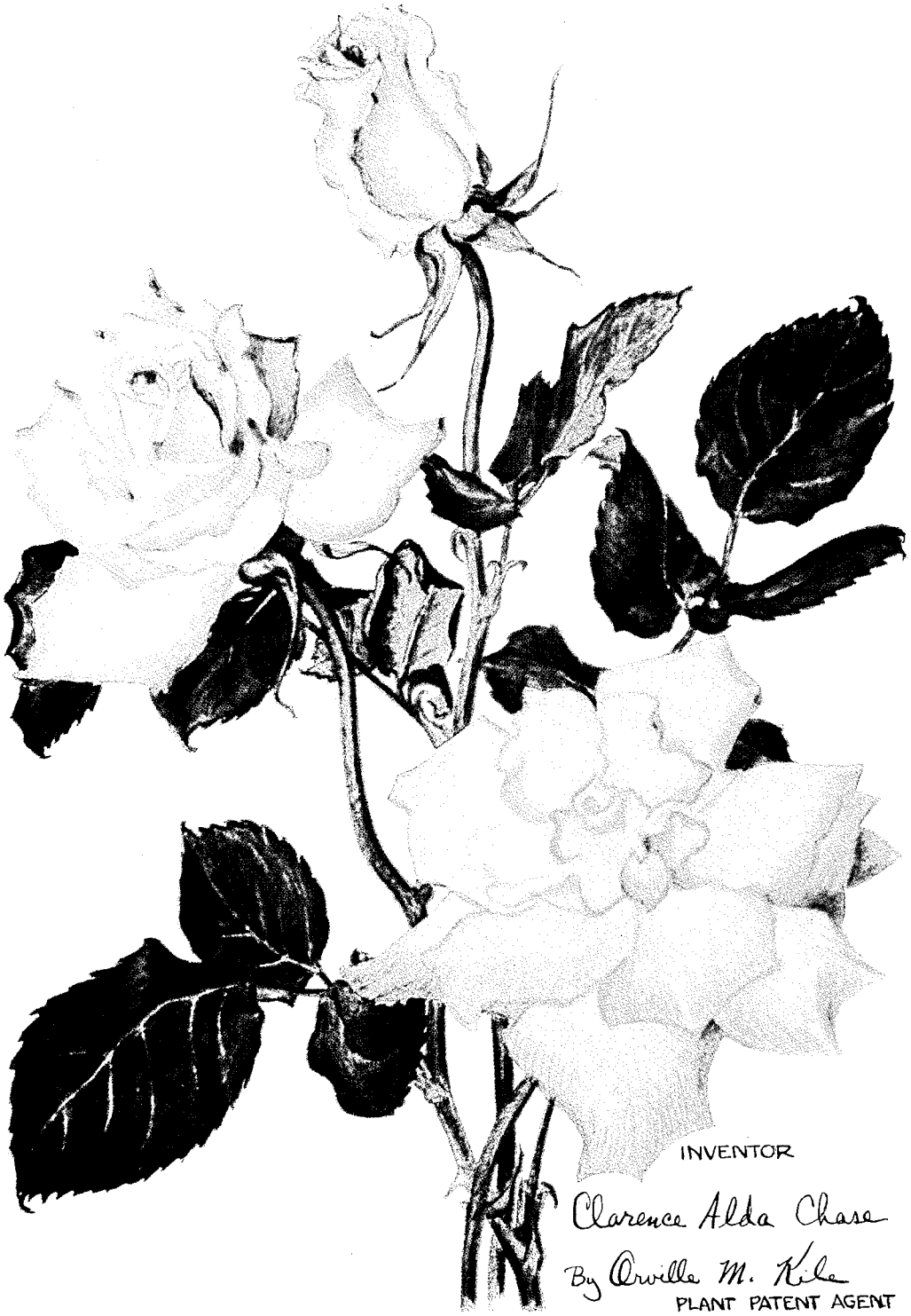
INVENTOR
Clarence Alda Chase
By Orville M. Kile
PLANT PATENT AGENT Patented Apr. 30, 1940

Plant Pat. 383

UNITED STATES PATENT OFFICE

383

ROSE

Clarence Alda Chase, Lane County, Oreg.

Application June 20, 1939, Serial No. 280,154

1 Claim. (Cl. 47—61)

My present discovery relates to improvements in hybrid tea roses of the bush type and was discovered by me in the greenhouses of Chase Gardens as a sporting branch growing from a Rapture Plant. The new sport variety is much like the parent variety in many respects, particularly in its vigorous growth. The feature which immediately distinguishes my new variety from its parent is the greatly increased depth and brilliance of the color of the blossoms of the new variety and the translucence of its petals. The complete change in the appearance of the flower in its different stages is also very notable—the opening flower and fully opened flower being scarcely recognizable as belonging to the same variety. Other features which help to distinguish this variety from its parent variety are the slightly larger bud and the abundant foliage of a darker shade.

This new variety has been asexually reproduced and the new plants show the same distinguishing characteristics as the original sport.

The original illustrations accompanying this application show in approximately their true colors a bud, a partly opened bloom and a bloom soon after becoming fully opened. It must be understood, however, that it is difficult for the artist to show the brilliance and glow which is an important feature of the coloring of the opening bloom of this variety.

In the following detailed description of this new variety of rose, color plate references indicate Ridgway's Color Standards and Nomenclature. Where no color plate references are given, the ordinary dictionary term is intended.

*The plant*

Growth: Very vigorous.

Form: Upright bush.

Disease resistance: Very resistant to common rose diseases.

Foliage: Very abundant.

*Leaves.*—Compound, 3 to 7 leaflets.

*Leaflets.*—Shape—oval with acuminate apex and rounded base. Size—terminal leaflet averages 2½ by 1¾ inches. Others are gradually smaller toward stem. Texture—heavy and leathery. Edge—singly serrated; indentations shallow. Color—Upper surface is between Dark Dull Yellow-Green and Empire Green (Plate XXXII) but with a shiny aspect, and has midrib of lighter green. Under surface is Hellebore Green (Plate XVII), sometimes slightly tinged with red or purple. Edge is usually tinged with purplish red, from Indian Lake to Dahlia Carmine (Plate XXVI).

*Rachis.*—Usually smooth below but with occasional prickle; grooved above. Tinged with red on upper side and sometimes on under side.

*Stipules.*—Medium; clinging with the exception of the sharp points.

Stems: Exceptionally stiff and strong. Slightly zigzagged between joints rather than absolutely straight stems. Internodes rather short, bringing leaves close together. Cerro Green (Plate V). No prickles or hairs present but there are many thorns.

*Thorns.*—Many; medium size; sharp; straight; slightly downward pointing; pink-tinted.

*The flower*

Bud:

*Peduncle.*—Short; stiff; erect; Oil Green (Plate V); smooth.

*Shape.*—Ovoid at first, then becoming long urn-shaped.

*Size.*—Large.

*Color.*—Rose Red (Plate XII), with a brilliance bordering somewhat on Scarlet-Red (Plate I).

*Calyx.*—Small; smooth, approximately Cerro Green (Plate V).

*Sepals.*—Five; simple, moderately short; recurve to stem.

Bloom:

*Size.*—Large, attaining a spread of 4 to 4½ inches. The size is due to large size of the individual petals rather than to the number of petals.

*Borne.*—Singly.

*Form.*—High centered, retaining its shape. As the flower opens the petals turn backward into a triangular shape, thus giving the fully opened flower a star-like shape. The central petals cover the stamens until the flower is fully opened. Characteristic of the flower is the upright position taken by the petals in such a way as to show clearly the Lemon Chrome (Plate IV) aiglet in the opening flower and the Rose Pink (Plate XII) center in the aging flower.

*Color.*—The color of the half-opened flower is lighter than that of the bud and has a glowing brilliance. There is no color in Ridgway's Color Standards which describes it. The color effect is much lighter than Rose Red (Plate XII), tends somewhat toward Spinel Pink (Plate XXVI), but is very much more brilliant and glowing than either. There is an aiglet of Lemon Chrome (Plate IV) which is larger on the inner surface of the petals than on the outer, and which does not diffuse upward.

When the flower is fully opened, the color again changes. The outer surface is then Rose Color (Plate XII), lightening slightly toward the base. The inner surface ranges from Rose Color (Plate XII) on the edges of the petals to Rose Pink (Plate XII) in the center, with a small aiglet of Lemon Chrome (Plate IV). The veining becomes much more prominent on the inner surface at this stage of development.

As the opened flower ages, the center of the petals fades until it is almost white. The point of each outer petal is Rose Color (Plate XII), the rest of the edge being slightly lighter. At this stage the Lemon Chrome (Plate IV) aiglet has practically disappeared.

*Petalage.*—Double, 18 to 20 petals in May. Petals are arranged regularly in three rows of five each and the remaining small petals are massed irregularly in the center. Petals—shape, obovate. In the bud stage there is a point at the top of many of the outer petals and the edges appear somewhat fluted. Later the petals roll backward into triangular shape, giving them an entirely different pointed effect. Appearance—silky and translucent in early stages; later opaque. Texture—substance seems to increase as flower ages. Persistence—Drop off cleanly after several days. Fragrance—unusually fragrant. Lasting quality—exceptionally good.

*Reproductive organs*

Stamens: Many; attached to outer portion of ovary and curved inwardly to encircle the bunched pistils.

*Filaments.*—Varying lengths; red, approaching Nopal Red (Plate I).

*Anthers.*—Large; between Apricot Yellow (Plate IV) and Deep Chrome (Plate III), turning brown as the flower ages.

*Pollen.*—Empire Yellow (Plate IV).

Pistils: Very many; bunched and protruding from the top of a hard, flat-topped ovary.

*Styles.*—Short; closely bunched; white.

*Stigmas.*—Red with top between Orange and Xanthine Orange (Plate III).

Ovary: Mostly inclosed.

Hips: Small.

Having thus disclosed my discovery, I claim:

A new and useful variety of hybrid tea rose with qualities in combination substantially as shown and described, characterized particularly by its large bud; its abundant and very dark green foliage; and its blossoms having intense and lasting fragrance and a deep glowing pink to rose red color which changes to rose color and rose pink as indicated.

CLARENCE ALDA CHASE.